United States Patent
Hoshi (10) Patent No.: US 8,946,327 B2
(45) Date of Patent: Feb. 3, 2015

(54) METHOD FOR PRODUCING SYNTHETIC AMYLOSPHEROID

(71) Applicant: Tao Health Life Pharma., Ltd., Kyoto (JP)

(72) Inventor: Minako Hoshi, Kyoto (JP)

(73) Assignee: Tao Health Life Pharma Co., Ltd., Kyoto (JP)

( * ) Notice: Subject to any disclaimer, the term of this patent is extended or adjusted under 35 U.S.C. 154(b) by 0 days.

(21) Appl. No.: 14/347,049

(22) PCT Filed: Dec. 18, 2012

(86) PCT No.: PCT/JP2012/082831
§ 371 (c)(1),
(2) Date: Mar. 25, 2014

(87) PCT Pub. No.: WO2013/094614
PCT Pub. Date: Jun. 27, 2013

(65) Prior Publication Data
US 2014/0350229 A1    Nov. 27, 2014

(30) Foreign Application Priority Data
Dec. 22, 2011    (JP) .................................. 2011-281845

(51) Int. Cl.
| C08F 236/12 | (2006.01) |
| G01N 33/00 | (2006.01) |
| G01N 33/44 | (2006.01) |
| C07K 14/47 | (2006.01) |

(52) U.S. Cl.
CPC .......... C07K 14/4711 (2013.01); *Y10S 530/812* (2013.01)
USPC ................ 524/297; 530/812; 436/86; 436/85

(58) Field of Classification Search
None
See application file for complete search history.

(56) References Cited

U.S. PATENT DOCUMENTS

| 8,168,188 B1 | 5/2012 | Hoshi et al. |
| 2010/0297662 A1 | 11/2010 | Hoshi et al. |

FOREIGN PATENT DOCUMENTS

| JP | 2006-342108 | 12/2006 |
| WO | 2006/016644 | 2/2006 |
| WO | 2009/057664 | 5/2009 |

OTHER PUBLICATIONS

Tokuraku et al., Real-Time Imaging and Quantification of Amyloid-beta Peptide Aggregates by Novel Quantum-Dot Nanoprobes. PLoS One Dec. 2009 | vol. 4 | Issue 12 | e8492, 1-11.*
Grant et al., "Familial Alzheimer's disease mutations alter the stability of the amyloid β-protein monomer folding nucleus", PNAS, Oct. 2007, vol. 104, No. 42, pp. 16522-16527.
International Search Report dated Feb. 5, 2013 issued in International (PCT) Application No. PCT/JP2012/082831.

(Continued)

*Primary Examiner* — Gregory S Emch
*Assistant Examiner* — Aurora M Fontainhas
(74) *Attorney, Agent, or Firm* — Wenderoth, Lind & Ponack, L.L.P.

(57) ABSTRACT

Provided is a method for producing synthetic amylospheroids efficiently, the method including agitating a liquid containing amyloid β-peptides in the presence of a plasticizer. Amylospheroid refers to an assembly of amyloid β-peptides that selectively can induce cell death of functionally mature neurons. Amylospheroid is considered to play a central role in the development of Alzheimer's disease and dementia with Lewy bodies.

3 Claims, 3 Drawing Sheets

(56) References Cited

OTHER PUBLICATIONS

A. Noguchi et al., "Isolation and Characterization of Patient-Derived, Toxic, High Mass Amyloid β-Protein (Aβ) Assembly from Alzheimer Disease Brains", The Journal of Biological Chemistry, vol. 284, No. 47, pp. 32895-32905, Nov. 20, 2009.

G. M. Shankar et al., "Amyloid-β Protein Dimers Isolated Directly from Alzheimer's Brains Impair Synaptic Plasticity and Memory", Nature Medicine, vol. 14, No. 8, pp. 837-842, Aug. 2008.

M. Hoshi et al., "Spherical Aggregates of β-Amyloid (Amylospheroid) Show High Neurotoxicity and Activate Tau Protein Kinase I/Glycogen Synthase Kinase-3β", PNAS, vol. 100, No. 11, pp. 6370-6375, May 27, 2003.

S. Matsumura et al., "Two Distinct Amyloid β-Protein (Aβ) Assembly Pathways Leading to Oligomers and Fibrils Identified by Combined Fluorescence Correlation Spectroscopy, Morphology, and Toxicity Analyses", Journal of Biological Chemistry, vol. 286, No. 13, pp. 11555-11562, Apr. 1, 2011.

\* cited by examiner

FIG. 4

METHOD FOR PRODUCING SYNTHETIC AMYLOSPHEROID

TECHNICAL FIELD

The present disclosure relates to a method for producing synthetic amylospheroids.

BACKGROUND ART

Alzheimer's disease is a disease that causes mature neurons to die via synaptic impairment. According to recent studies, Alzheimer's disease has found to develop stepwise. As the first stage, there is a stage in which synaptic impairment occurs chiefly, which is a reversible stage. As a stage subsequent to the reversible stage, there is a stage in which neuronal death occurs, which is an irreversible stage. It is considered that reaching this irreversible stage triggers the onset of Alzheimer's disease (Non-Patent Document 1).

The synaptic impairment is considered to occur mainly by the action of accumulated β amyloid (Aβ) dimers and dodecamers on glutamate receptors, and the like. However, neither Aβ dimers nor Aβ dodecamers induce neuronal death in vitro or in vivo (Non-Patent Document 2). Therefore, in order to analyze pathology of human Alzheimer's disease, it is necessary to clarify the cause and molecular mechanism of the neuronal death, which occurs in the irreversible stage subsequent to the reversible synaptic impairment stage.

Amylospheroids (ASPD) are unique Aβ assemblies that are toxic to neither non-neuronal cells nor immature neurons, but selectively cause functionally mature neurons to die (Non-Patent Document 1). First, amylospheroids were isolated as spherical Aβ assemblies about 10 nm in diameter, which cause neuronal death in vitro (Non-Patent Document 3). Later, antibodies specific to these synthetic amylospheroids were prepared (Patent Documents 1 and 2). Using these antibodies, amylospheroids formed in living bodies in brains of human patients with Alzheimer's disease (i.e., native amylospheroids) were isolated (Non-Patent Document 3). Based on studies using the native amylospheroids, the following have been clarified (Non-Patent Document 3): i) similarly to synthetic amylospheroids, native amylospheroids selectively induce cell death with respect to mature neurons; in correlation with the severity of Alzheimer's disease, the amount of native amylospheroids increases in cerebral cortex of patients with Alzheimer's disease with neuronal loss; and in cerebellum of patients with Alzheimer's disease with few neuronal loss, the amount of native amylospheroids is very small. Therefore, it is considered that amylospheroids play a central role in the irreversible stage that triggers the onset of Alzheimer's disease. Moreover, native amylospheroids are detected also in brains of patients with dementia with Lewy bodies (Non-Patent Document 1). Hence, it is considered that amylospheroids play a central role also in the onset of dementia with Lewy bodies.

Incidentally, although the amylospheroids and the Aβ dimers and Aβ dodecamers, which are considered as the main cause of synaptic impairment, are both Aβ assemblies, it is indicated that they are formed from Aβ monomers via different paths. Specifically, Aβ dimers and Aβ dodecamers are formed via Aβ dimers, whereas amylospheroids are formed from Aβ trimers (Non-Patent Document 4).

PRIOR ART DOCUMENTS

Patent Documents

Patent Document 1: WO2006/016644
Patent Document 2: WO2009/057664

Non-Patent Documents

Non-Patent Document 1: Noguchi et al., J. Biol. Chem., vol. 284, no. 47, 32895-32905 (2009)
Non-Patent Document 2: Shankar et al., Nature Medicine 14, 837-842 (2008)
Non-Patent Document 3: Hoshi et al., Pro. Natl. Acad. Sci., U.S.A., vol. 100, no. 11, 6370-6375 (2003)
Non-Patent Document 4: Matsumura et al., J. Biol. Chem., vol. 286, no. 13, 11555-11562 (2011)

DISCLOSURE OF INVENTION

Problem to be Solved by the Invention

As described above, amylospheroids play a central role in Alzheimer's disease and dementia with Lewy bodies. However, it is very difficult to purify native amylospheroids from brains of patients and using them for developing therapeutic agents, etc. Therefore, if synthetic amylospheroids that are equivalent to native amylospheroids exist in brains of patients are produced easily in vitro, this will greatly contribute to studies of Alzheimer's disease and dementia with Lewy bodies, developments of preventive methods and preventive agents against these diseases, and developments of therapeutic methods and preventive/therapeutic agents. For example, this will allow us to develop active immunization therapy in which synthetic amylospheroids themselves are used as antigens, and to get closer to the molecular mechanism of neuronal death, thereby facilitating development of inhibitors of neuronal death. Further, at present, since the formation mechanism of aggregates in human brains is unknown, it becomes possible to develop preventive agents that inhibit the formation of amylospheroids by utilizing the formation of synthetic amylospheroids as a model system.

With the foregoing in mind, the present disclosure provides a method for producing synthetic amylospheroids efficiently.

Means for Solving Problem

In one aspect, the present disclosure relates to a method for producing synthetic amylospheroids, including agitating a liquid containing amyloid β-peptides in the presence of a plasticizer (hereinafter, referred to as "production method of the present disclosure").

Effect of the Invention

According to the production method of the present disclosure, it is possible to improve efficiency of producing synthetic amylospheroids.

DESCRIPTION OF THE INVENTION

The present disclosure is based on the finding that, when synthetic amylospheroids are formed by agitating a liquid containing amyloid β-peptides, the presence of a plasticizer in the solution significantly improves the formation efficiency. In other words, the present disclosure is based on the finding that, in the presence of the plasticizer, performing the agitation in the conventional production method of synthetic ASPD described in Non-Patent Documents 1 and 3 significantly improves the formation efficiency of synthetic amylospheroids.

Although details are unknown about the mechanism that the presence of the plasticizer improves the formation efficiency of synthetic amylospheroids, they are considered as follows. Amyloid β normally is stable as a monomer (Grant M A et al., PNAS 104, 16522-16527, 2007). Further, it is known that when amyloid p forms fibrils, amyloid β dimers are formed first, and when amyloid β forms amylospheroids, amyloid β trimers are formed first (Matsumura et al., JBC2011, Non-Patent Document 4). It also is known that, unlike the formation of fibrils, the formation of amylospheroids is promoted in the presence of a solute that has a specific partial structure such as phosphoric acid in a physiological solvent environment (Hosni et al., data presented in academic conferences). Therefore, by interacting with amyloid β-monomers, the plasticizer exhibits an effect of promoting the formation of trimers, particularly the formation of amylospheroids. The present discloser may not be limited to this mechanism. Incidentally, in the present specification, "formation efficiency of synthetic amylospheroids" can be, for example, a ratio of the amount of amyloid β-peptides contained in produced synthetic amylospheroids with respect to the amount of used amyloid β-peptides (the amount of Aβ forming synthetic ASPD/the amount of Aβ as starting material). The ratio may be either a weight ratio, or a molar ratio.

[Amylospheroid]

In the present specification, amylospheroid (hereinafter, also called "ASPD") refers to an Aβ assembly that selectively can induce cell death of functionally mature neurons. The ASPD includes "synthetic ASPD" and "native ASPD". The synthetic ASPD (synthetic amylospheroid) refers to ASPD having a spherical body about 10 to 15 nm in diameter in electron microscope observation, which can be prepared and isolated in vitro using synthetic Aβ (Non-Patent Document 3). The native ASPD refers to ASPD that can be isolated from human living bodies (especially, brains of patients with Alzheimer's disease and/or dementia with Lewy bodies (Non-Patent Document 1). Both of the synthetic ASPD and the native ASPD induce cell death of mature human neurons. Further, anti-ASPD antibodies (monoclonal antibody and polyclonal antibody) also have been produced that can recognize a tertiary structure specific to ASPD (e.g., haASD1, haASD2, mASD3, etc., disclosed in Patent Documents 1 and 2). According to results of characteristic analysis of anti-ASPD monoclonal antibodies and NMR analysis of ASPD, ASPD is known to have a unique tertiary structure that is different from those of conventionally reported other Aβ assemblies (e.g., Non-Patent Document 1, Supplemental Table S1). Therefore, in the present specification, ASPD also can refer to an Aβ assembly that reacts with an anti-ASPD antibody specific to ASPD disclosed in Patent Documents 1 and 2 and that selectively can induce cell death of functionally mature neurons.

[Amyloid β-Peptide]

In the present specification, "amyloid β-peptide" refers to a peptide that is cut out by cleavage of an amyloid precursor protein (APP) by α-, β-, and γ-secretases, and is indicated also as "β amyloid", "Aβ", or "Aβ peptide". Further, in the present specification, Aβ may be amyloid β-peptides that are called $A\beta_{1-39}$, $A\beta_{1-40}$, $A\beta_{1-41}$, $A\beta_{1-42}$, and $A\beta_{1-43}$ based on the length of the amino acid sequence. In the present specification, Aβ may be either a human type (sequences existing in humans), or a nonhuman type (sequences existing in animals other than humans). Further, in the present specification, Aβ may be Aβ in living bodies (native Aβ) and synthetic Aβ. Though not limited particularly, the synthetic Aβ can be synthesized by a known peptide synthesis method (e.g., Fmoc method and Boc method), and can be produced using a known peptide synthesizer, for example. The human-type $A\beta_{1-42}$ (also called "Aβ42") is a peptide having an amino acid sequence represented by DAEFRHDSGYEVHHQKLVFFAEDVGSNK-GAIIGLMVGGVVIA (SEQ ID NO: 1). Further, the human-type $A\beta_{1-41}$ (Aβ41), $A\beta_{1-40}$ (Aβ40), and $A\beta_{1-39}$ (Aβ39) are a peptide having an amino acid sequence represented by SEQ ID NO: 1 which has been deleted A, IA, and VIA from the C-terminal, respectively. Moreover, the human-type $A\beta_{1-43}$ (Aβ43) is a peptide having an amino acid sequence represented by SEQ ID NO: 1 to the C-terminal of which has been added one threonine residue (T/Thr).

[Plasticizer]

In the present specification, "plasticizer" is not limited particularly, examples of which include known plasticizers. In terms of improving the formation efficiency of synthetic ASPD, preferable examples of the plasticizer to be used in the production method of the present disclosure include: phthalate esters such as di-n-octyl phthalate, di-2-ethylhexyl phthalate (DEHP), dibenzyl phthalate, and diisodecyl phthalate; isophthalate esters such as dioctyl isophthalate; adipate esters such as di-n-butyl adipate and dioctyl adipate; maleate esters such as di-n-butyl maleate; citrate esters such as acetyl tri-n-butyl citrate; itaconate esters such as monobutyl itaconate; oleate esters such as butyl oleate; polyhydric alcohol esters such as diacetyl caprylic acid monoglyceride, diacetyl lauric acid monoglyceride, ricinoleic acid monoglyceride, and decaglycerol monooleate; phosphate esters such as tricresyl phosphate; polyalkylene glycols such as polyethylene glycol (hereinafter, PEG), PEG diacetate, polypropylene glycol (hereinafter, PPG), PEG-PPG-PEG block polymer, and PPG-PEG-PPG block polymer; lactic acid oligomer esters such as triethylene glycol monomethyl ether lactic acid oligomer ester; rosinate esters such as diethylene glycol rosinate ester acetate. Among these, in terms of the same reason, the plasticizer is more preferably phthalate esters such as di-n-octyl phthalate, di-2-ethylhexyl phthalate, dibenzyl phthalate, diisodecyl phthalate, and further preferably di-2-ethylhexyl phthalate.

[Agitation]

In the present specification, "agitation" refers to the act of adding motion to fluids. In the present discloser, "agitation" is preferably low-speed and/or gentle agitation, so as not to prevent aggregation of Aβ and/or formation of ASPD. The agitation in the present disclosure may be performed by moving a vessel that holds a liquid containing Aβ, for example, by adding motion such as rotation, shaking, vibration, and combination of these, to the vessel, or may be performed by arranging a stirrer in the liquid containing Aβ and rotating the stirrer. As described above, the agitation strength is preferably low speed and/or gentle, and may be comparable to the agitation strength in the conventional production method of synthetic ASPD described in Non-Patent Documents 1 and 3. Moreover, the agitation in the production method of the present disclosure may be performed continuously within a predetermined time, or may be performed intermittently.

[Formation of Synthetic ASPD]

The production method of the present disclosure includes agitating a liquid containing Aβ in the presence of a plasticizer. It is considered that synthetic ASPD is formed by aggregation or association of the above-described Aβ during the agitation. Therefore, in one embodiment, the production method of the present disclosure includes a step of forming synthetic ASPD, the step including agitating the liquid containing Aβ and plasticizer.

The content of Aβ in the liquid containing Aβ and plasticizer for use in the formation step of synthetic ASPD is preferably 0.1 to 500 µM, more preferably 1 to 350 µM, further preferably 10 to 200 µM, further more preferably 20 to 100 µM, further more preferably 30 to 75 µM, and further more preferably 40 to 60 µM, in terms of improving the formation efficiency of synthetic ASPD. The Aβ contained in the liquid is preferably a monomer, i.e., no formation of Aβ assemblies before the formation step of synthetic ASPD, in terms of improving the formation efficiency of synthetic ASPD. Further, the Aβ contained in the liquid may be either one kind, or a mixture of two or more kinds. For example, the Aβ contained in the liquid may be either one kind, Aβ42 or Aβ40, or a mixture of Aβ42 and Aβ40.

The content of the plasticizer in the liquid containing Aβ and plasticizer for use in the formation step of synthetic ASPD is preferably 10 µM to 10 mM, more preferably 100 to 1000 µM, further preferably 200 to 900 µM, further more preferably 400 to 800 µM, further more preferably 500 to 750 µM, and further more preferably 600 to 700 µM, in terms of improving the formation efficiency of synthetic ASPD. The plasticizer contained in the liquid may be either one kind, or a mixture of two or more kinds.

The agitation temperature in the formation step of synthetic ASPD is preferably more than 0° C. to 40° C. or lower, more preferably 37° C. or lower, further preferably 32° C. or lower, further more preferably 12° C. or lower, and further more preferably 5° C. or lower, in terms of improving the formation efficiency of synthetic ASPD. In the present specification, the "agitation temperature" refers to an environmental temperature or an ambient temperature at which the agitation is performed.

The agitation time in the formation step of synthetic ASPD is 10 hours to 8 days, for example. When the Aβ contained in the liquid for use in the step is Aβ42, the agitation time is preferably 10 to 20 hours, more preferably 11 to 18 hours, further preferably 12 to 16 hours, and further more preferably 13 to 15 hours, in terms of improving the formation efficiency of synthetic ASPD. When the Aβ is Aβ40, the agitation time is preferably 4 to 8 days, and more preferably 5 to 7 days, in terms of improving the formation efficiency of synthetic ASPD. When the Aβ is other than these or a mixture of these, the agitation time can be adjusted appropriately within the above-described range.

[Confirmation of Formation of Synthetic ASPD]

The formation of synthetic ASPD by the production method of the present disclosure or the above-described formation step of synthetic ASPD can be confirmed by checking its cytotoxicity and/or antibody reactivity. For example, the presence of ASPD can be confirmed if cell death (apoptosis) can be induced when adding the obtained synthetic ASPD to mature neurons (Non-Patent Documents 1 and 3). Alternatively, the presence of ASPD can be confirmed using antibodies specific to ASPD. Examples of the antibodies include monoclonal antibodies specific to ASPD such as haASD1, haASD2 and mASD3 disclosed in Patent Documents 1 and 2, and polyclonal antibodies specific to ASPD such as rpASD1. With use of these antibodies, it is possible to quantify synthetic ASPD in accordance with conventionally known methods.

[Purification of Synthetic ASPD]

The synthetic ASPD formed by the production method of the present disclosure or the above-described formation step of synthetic ASPD can be purified by filtering a liquid after agitation using a filter with a pore diameter of 0.22 µm, filtering the filtrate through an ultrafilter with a cutoff of 50 kDa or 100 kDa, and collecting residues. Alternatively, the synthetic ASPD can be purified by an immunoprecipitation method using antibodies specific to ASPD, such as antibodies disclosed in the above-described Patent Document 1 or 2. The production method of the present disclosure may include a step of purifying formed synthetic ASPD. The purification method of synthetic ASPD is not limited to this method.

[Preparation of Liquid Containing Aβ and Plasticizer]

In the production method of the present disclosure, the liquid containing Aβ and plasticizer for use in the agitation is preferably prepared by a method that includes: dissolving Aβ in an organic solvent containing a plasticizer; and diluting the obtained Aβ solution with an aqueous solution, in terms of improving the formation efficiency of synthetic ASPD. Therefore, in another embodiment, the production method of the present disclosure relates to a production method of synthetic ASPD that includes: 1) a preparation step of a liquid containing Aβ and plasticizer; and 2) a formation step of synthetic ASPD, wherein the step 1) includes dissolving Aβ in an organic solvent containing a plasticizer; and diluting the obtained Aβ solution with an aqueous solution, and the step 2) includes agitating the liquid containing Aβ and plasticizer obtained in the above-described step 1).

The Aβ to be dissolved in the organic solvent containing the plasticizer is preferably lyophilized, in terms of improving the formation efficiency of synthetic ASPD. The organic solvent is preferably an organic solvent that can dissolve Aβ and plasticizer and is water miscible, more preferably an organic solvent selected from N,N-dimethylformamide (DMF), N,N-dimethylacetamide (DMAc), tetrahydrofuran (THF), dimethyl sulfoxide (DMSO), acetone, and a mixture of these, further preferably dimethyl sulfoxide (DMSO), and further more preferably anhydrous DMSO, in terms of improving the formation efficiency of synthetic ASPD.

The concentration of the plasticizer in the organic solvent containing the plasticizer can be determined appropriately by the dilution ratio adjusted using the aqueous solution to be described later, and the concentration of the plasticizer in the liquid containing Aβ and plasticizer described above.

As the aqueous solution to be used for dilution, conventionally known buffer solutions and cell culture mediums can be used. The aqueous solution is preferably an aqueous solution that has a physiological ionic strength and pH, in terms of improving the formation efficiency of synthetic ASPD.

Preferable examples of the buffer solution to be used as the aqueous solution include phosphate buffered saline (PBS), a solution of buffer having a tris(hydroxymethyl)methyl moiety ((HOCH$_2$)$_3$C-moiety), a 2-(hydroxymethyl)-1,3-propanediol (HMPD) solution, and a 1,3-propanediol solution, in terms of improving the formation efficiency of synthetic ASPD. Incidentally, examples of the buffer having the tris (hydroxymethyl)methyl moiety include N-Tris(hydroxymethyl)methyl-2-aminoethanesulfonic acid (TES), tris(hydroxymethyl)aminomethane (Tris), N-[Tris(hydroxymethyl)methyl]glycine (Tricine), N-Tris(hydroxymethyl)methyl-3-aminopropanesulfonic acid (TAPS) and 1,1,1-tris (hydroxymethyl)ethane (THME). The aqueous solution is more preferably PSB, and further preferably calcium- and magnesium-free Dulbecco's phosphate-buffered saline (D-PBS(−)), in terms of the same reason.

The cell culture medium to be used as the aqueous solution is preferably BME medium, BGJb medium, CMRL 1066 medium, Glasgow MEM medium, Improved MEM Zinc Option medium, IMDM medium, Medium 199 medium, Eagle MEM medium, αMEM medium, DMEM medium, Ham's F12 medium, RPMI 1640 medium, Fischer's medium, and mixed mediums of these, and more preferably mediums of these from which a pH indicator has been removed, in terms of improving the formation efficiency of synthetic ASPD. The aqueous solution is more preferably Ham's F12 medium, and further preferably L-glutamine- and phenol red-free Ham's F12 medium, in terms of the same reason.

The dilution ratio for diluting the Aβ solution with the aqueous solution is preferably 5 to 5000 times, more preferably 10 to 1000 times, further preferably 50 to 500 times, further more preferably 75 to 200 times, and further more preferably 90 to 120 times, in terms of improving the formation efficiency of synthetic ASPD.

[Pretreatment]

The Aβ for use in the above-described "Preparation of Liquid Containing Aβ and Plasticizer" is preferably subjected to a pretreatment that includes: dissolving Aβ in a volatile solvent; and lyophilizing it, in terms of improving the formation efficiency of synthetic ASPD and inducing a-helix in Aβ. Further, in terms of the same reason, the pretreatment is preferably performed 2 to 3 cycles, one cycle including: dissolving powdered or lyophilized Aβ in a volatile solvent; and lyophilizing it. In the first cycle, in order to dissolve Aβ perfectly, Aβ is preferably dissolved in the volatile solvent and thereafter incubated. Preferably, the incubation is performed overnight (e.g., 6 to 12 hours) at 2 to 8° C. (preferably about 4° C.) and thereafter for 30 minutes to 4 hours (preferably about 2 hours) at 25 to 40° C. (preferably about 37° C.) for example, though not limited to this condition. Further, in one or a plurality of embodiments, preferably the incubation is performed in two stages, the first incubation being performed at 2 to 8° C. and the second incubation being performed at 25 to 40° C. The temperature of the first incubation is 2 to 8° C., and preferably about 4° C. The time of the first incubation is overnight, and preferably 6 to 12 hours, for example. The temperature of the second incubation is 25 to 40° C., and preferably about 37° C. The time of the second incubation is 30 minutes to 4 hours, and preferably about 2 hours, for example.

The volatile solvent to be used in the pretreatment is preferably methylene chloride, acetone, 1,1,1,3,3,3-hexafluoro-2-propanol (HFIP), tetrahydrofuran (THF), and a combination of these, and more preferably HFIP, in terms of improving the formation efficiency of synthetic ASPD and inducing a-helix in Aβ.

[Reagent Kit]

In another aspect, the present disclosure relates to a reagent kit for producing synthetic ASPD by the production method of the present disclosure, which includes: lyophilized Aβ; the above-described organic solvent; and the above-described plasticizer. Preferably, the lyophilized Aβ has been subjected to the above-described pretreatment. According to the reagent kit of the present disclosure, it is possible to easily perform the above-described "Preparation of Liquid Containing Aβ and Plasticizer", which still further facilitates implementation of the production method of the present disclosure.

EXAMPLES

Example 1

To an Aβ42 starting material in a lyophilized state (Ca. 50 nmol/tube) prepared under the following conditions, 10 μL of a DMSO solution containing 65 mM bis(2-ethylhexyl)phthalate (DEHP) prepared as below was added for dissolving the starting material, whereby a 5 mM Aβ solution was obtained. To the 5 mM Aβ solution, 990 μL of an L-glutamine- and phenol red-free F12 buffer (manufactured by Kohjin Bio Co., Ltd.) was added, whereby a 50 μM Aβ solution was obtained. The 50 μM Aβ solution was rotationally agitated at 4° C. for 14 hours using a rotator. Thus, synthetic ASPD was formed. From the solution containing formed synthetic ASPD, synthetic ASPD was purified under the following conditions. The formation efficiency of synthetic ASPD of the purified synthetic ASPD calculated under the following conditions was 57% (in terms of monomer). Incidentally, the formation of synthetic ASPD was confirmed by electron microscope observation, dot blot using anti-ASPD antibodies, and amino acid analysis. Finally, neurotoxicity of the obtained synthetic ASPD was checked by the cytotoxicity test under the following conditions.

[Preparation Method of Aβ42 Starting Material]

Aβ42 peptides having an amino acid sequence represented by SEQ ID NO: 1 in the Sequence Listing were synthesized by the Fmoc method using a peptide synthesizer (model 433A, manufactured by Applied Biosystems), followed by purification. To about 50 mg of Aβ42 peptides after lyophilization, 100 mL of HFIP (1,1,1,3,3,3-hexafluoro-2-propanol, for HPLC, manufactured by KANTO CHEMICAL CO., INC.) was added for dissolving the peptides. The obtained solution was incubated overnight at 4° C., incubated for 3 hours at 37° C., dispensed into tubes per 500 μL, and stocked at −80° C. After lyophilization of the stocked Aβ42 solution, 500 μL of HFIP was added thereto again for dissolving the Aβ42 (Aβ42 concentration, Ca. 100 μM). The solution was lyophilized again, and stocked at −20° C. Thus, an Aβ42 starting material was obtained.

[Preparation of 65 mM DEHP/DMSO Solution]

To 75.7 μL of anhydrous DMSO (dimethyl sulfoxide anhydrous, manufactured by Sigma-Aldrich), 2 μL of DEHP (bis (2-ethylhexyl)phthalate, manufactured by TOKYO CHEMICAL INDUSTRY CO., LTD.) was added. Thus, a 65 mM DEHP/DMSO solution was obtained.

[Purification Conditions of Synthetic ASPD]

500 μL of a synthetic ASPD solution after rotary agitation was filtered through a filter with a pore diameter of 0.22 μm, the filtrate was filtered through an ultrafilter with a cutoff of 100 kDa or 50 kDa, and residues were collected. Thus, "158-669 kDa synthetic ASPD fraction" was obtained.

[Measurement Conditions of ASPD Formation Efficiency (Calculation Method)]

In order to examine the ASPD formation efficiency, the amount of ASPD purified in the above-described manner was calculated by a dot blot method using rabbit polyclonal anti-ASPD antibody (rpASD1), based on standard ASPD with a known concentration. In order to examine this further, the content of amyloid β was calculated by amino acid analysis.

[Cytotoxicity Test]

The formation of ASPD was confirmed by the following cytotoxicity test. A certain amount of ASPD was administered overnight to primary cultured neurons (more than 19 days after starting culture) derived from hippocampus of mature rat, and the neurotoxicity was measured in accordance with protocols using Cell Death Detection ELISA manufactured by Roche Diagnostics. This is an ELISA kit for quantitative detection of histone-complexed DNA fragmentation in the cells caused by apoptosis.

Comparative Example 1

Synthetic ASPD was produced from Aβ42 peptides in the same manner as in Example 1, except that anhydrous DMSO was used instead of the DMSO solution containing 65 mM DEHP. Consequently, the formation efficiency of synthetic ASPD was 1.2% (in terms of monomer).

Figure 1:
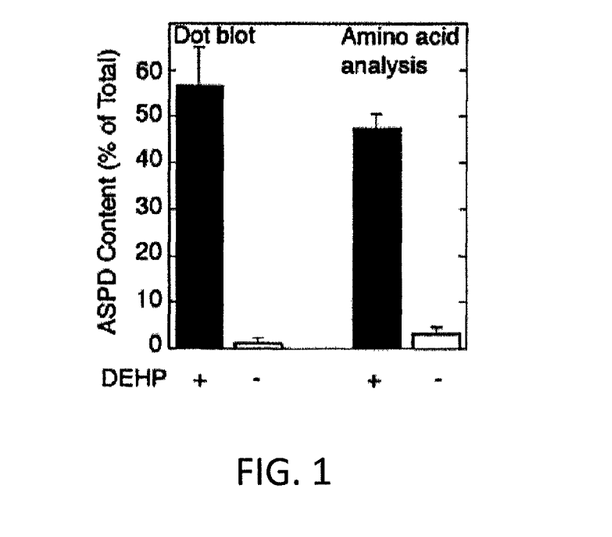
FIG. 1 is a graph showing exemplary measurement results of the ASPD formation efficiency in Example 1 (DEHP+) and Comparative Example 1 (DEHP−).

FIG. 1 shows exemplary results of the dot blot and amino acid analysis in Example 1 and Comparative Example 1. As shown in FIG. 1, the ASPD formation efficiency was improved significantly in Example 1 (DEHP+) as compared with Comparative Example 1 (DEHP−).

Figure 2:
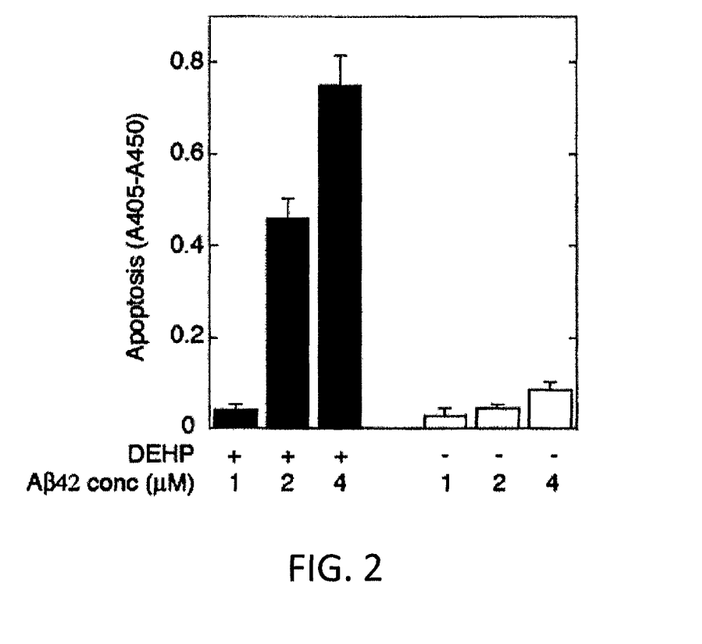
FIG. 2 is a graph showing exemplary results of the cytotoxicity test in Example 1 (DEHP+) and Comparative Example 1 (DEHP−).

Further, FIG. 2 shows exemplary results of the cytotoxicity test using the synthetic ASPD produced in Example 1 and the synthetic ASPD produced in Comparative Example 1. FIG. 2 shows results of the cytotoxicity test performed using the solution of Example 1 (DEHP+) and the solution of Comparative Example 1 (DEHP−) containing synthetic ASPD before purification, at concentrations of 1, 2 and 4 μM (in terms of Aβ42) shown in the figure. As shown in FIG. 2, the solution of Example 1 exhibited significant cytotoxicity in a concentration-dependent manner, as compared with the solution of Comparative Example 1. No cytotoxicity was found in the solution containing the same concentration of DEHP and not containing synthetic ASPD (data not shown).

Figure 3:
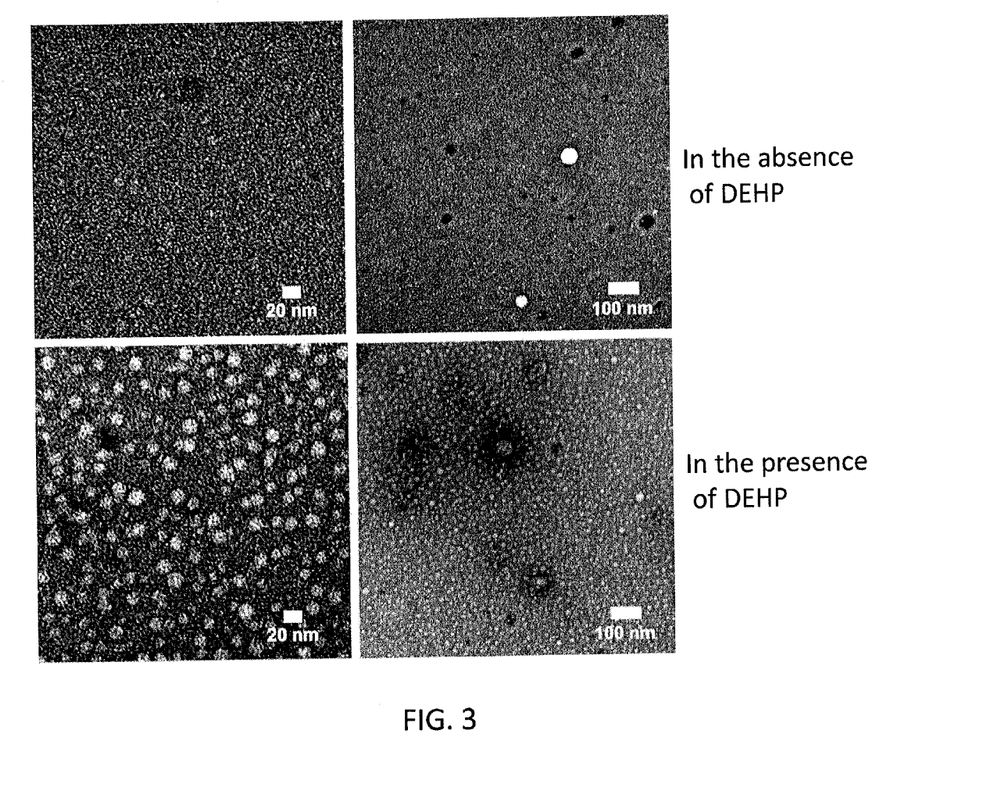
FIG. 3 shows exemplary micrographs taken through electron microscope observation in Example 1 (in the presence of DEHP) and Comparative Example 1 (in the absence of DEHP).

FIG. 3 shows exemplary micrographs of the solution of Example 1 (in the presence of DEHP) and the solution of Comparative Example 1 (in the absence of DEHP) containing synthetic ASPD before purification, taken through electron microscope observation. As shown in FIG. 3, in Example 1, as compared with Comparative Example 1, a large amount of synthetic ASPD having a spherical body about 10 to 15 nm in diameter was confirmed.

Examples 3-6

Figure 4:
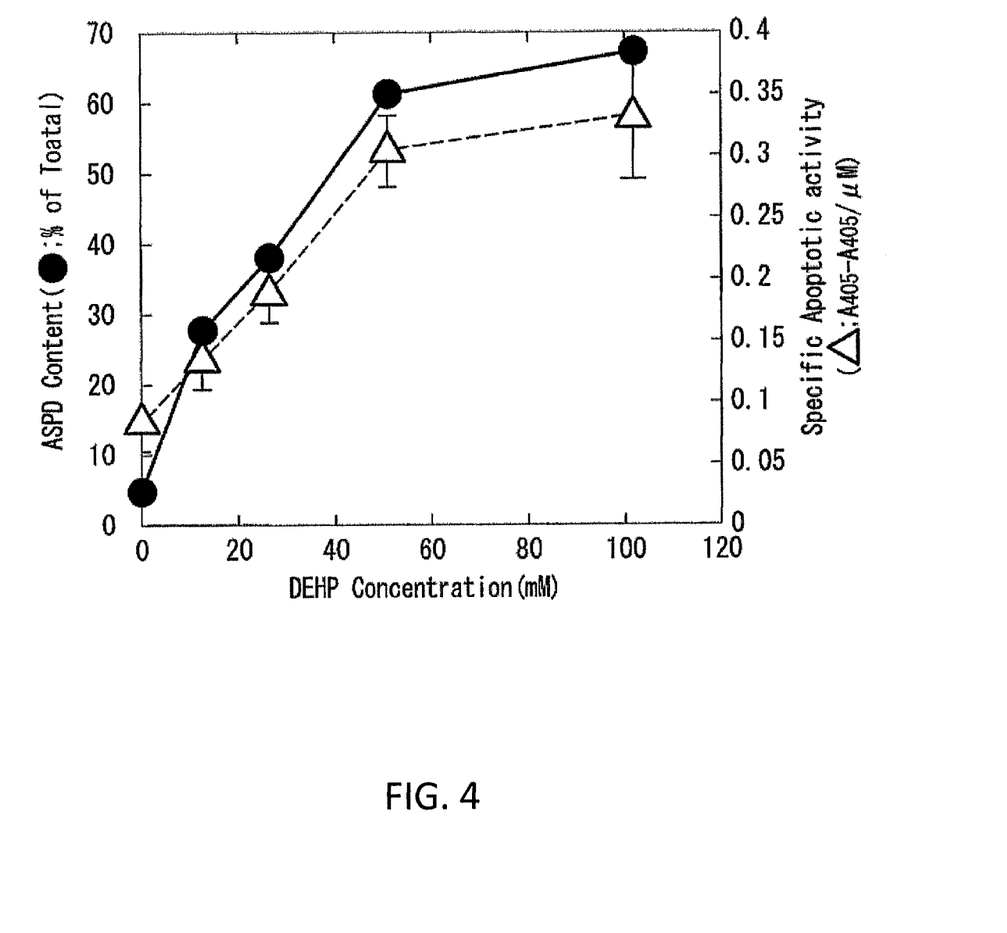
FIG. 4 is a graph showing exemplary results of the ASPD formation efficiency measurement and the cytotoxicity test in Examples 3-6 and Comparative Example 1.

Synthetic ASPDs of Examples 3-6 were produced from Aβ42 peptides in the same manner as in Example 1, except that the 65 mM DEHP/DMSO solutions of Examples 3-6 were adjusted to have the DEHP concentration of 13, 26, 51, and 102 mM, respectively. The ASPD formation efficiency measurement and the cytotoxicity test were performed in the same manner as in Example 1. Consequently, the formation efficiencies of the synthetic ASPDs of Examples 3-6 were 67%, 61%, 38%, and 28% (in terms of monomer), respectively. FIG. 4 shows exemplary results of the ASPD formation efficiency measurement and the cytotoxicity test in Comparative Example 1 and Examples 3-6 (the DEHP concentrations were 0, 13, 26, 51 and 102 mM, respectively). As shown in FIG. 4, the ASPD formation efficiency and cytotoxicity increased depending on the concentration of DEHP used in the formation of ASPD.

Industrial Applicability

The present disclosure is useful in, for example, the medical, pharmaceutical, and research fields related to Alzheimer's disease and/or dementia with Lewy bodies.

The invention claimed is:

1. A method for producing synthetic amylospheroid, comprising:
   agitating a liquid containing amyloid β-peptides in the presence of a plasticizer, wherein the plasticizer is a phthalate ester.

2. The method for producing synthetic amylospheroid according to claim 1, comprising:

dissolving amyloid β-peptides in an organic solvent containing the plasticizer;
diluting the solution of amyloid β-peptides with an aqueous solution; and agitating the solution after dilution.

3. The method for producing synthetic amylospheroid according to claim 2, wherein the organic solvent is a water-miscible solvent.

* * * * *

SEQUENCE LISTING

```
<160> NUMBER OF SEQ ID NOS: 1

<210> SEQ ID NO 1
<211> LENGTH: 42
<212> TYPE: PRT
<213> ORGANISM: Homo sapiens

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40
```